United States Patent
Shodai et al.

(10) Patent No.: US 6,632,452 B1
(45) Date of Patent: Oct. 14, 2003

(54) MEDICINAL COMPOSITIONS RETARDED IN THE DISCOLORATION OF PHENOLIC HYDROXYL COMPOUNDS

(75) Inventors: Hidekazu Shodai, Amagasaki (JP); Noboru Nagafuji, Sakai (JP); Shuichi Matsuda, Amagasaki (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/869,357

(22) PCT Filed: Jan. 14, 2000

(86) PCT No.: PCT/JP00/00154

§ 371 (c)(1),
(2), (4) Date: Jun. 28, 2001

(87) PCT Pub. No.: WO00/42997

PCT Pub. Date: Jul. 27, 2000

(30) Foreign Application Priority Data

Jan. 21, 1999 (JP) .............................. 11-012651

(51) Int. Cl.[7] .............................. A61K 9/10; A61K 9/20; A61K 47/12
(52) U.S. Cl. .................. 424/465; 424/484; 514/970
(58) Field of Search ................ 424/464, 10.3, 424/484, 465; 514/731, 970

(56) References Cited

U.S. PATENT DOCUMENTS

| 4,308,406 A | 12/1981 | Takenaka et al. | |
|---|---|---|---|
| 5,418,230 A | 5/1995 | Matsumoto et al. | 514/222.2 |
| 5,962,488 A | * 10/1999 | Lang | |
| 5,977,183 A | * 11/1999 | Scepanski | |

FOREIGN PATENT DOCUMENTS

| EP | 595546 | 5/1994 |
|---|---|---|
| JP | 57-188515 | 11/1982 |
| JP | 61-236710 | 10/1986 |
| JP | 63-145213 | 6/1988 |
| JP | 6-239716 | 8/1994 |
| JP | 63-145213 | 6/1998 |

* cited by examiner

Primary Examiner—Edward J Webman
(74) Attorney, Agent, or Firm—Wenderoth, Lind & Ponack, L.L.P.

(57) ABSTRACT

Coloring change of a pharmaceutical composition containing a compound having a phenolic hydroxyl group, such as an anti-inflammatory agent or an antioxidant having a phenolic hydroxyl group or the compound of formula (I) can be controlled by adding an acid. The present invention provides a pharmaceutical composition containing a compound having a phenolic hydroxyl group and an acid in which coloring change is controlled.

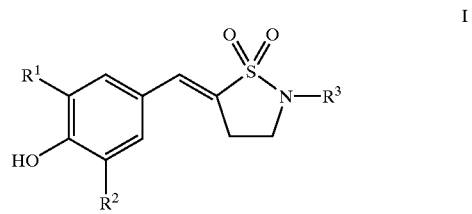

11 Claims, 1 Drawing Sheet

MEDICINAL COMPOSITIONS RETARDED IN THE DISCOLORATION OF PHENOLIC HYDROXYL COMPOUNDS

This application is a 371 of PCT/JP00/00154 filed Jan. 14, 2000.

TECHNICAL FIELD

This invention relates to a pharmaceutical composition containing a compound having a phenolic hydroxyl group with coloring change being controlled, in detail a pharmaceutical composition comprising an anti-inflammatory agent or an antioxidant having a phenolic hydroxyl group with coloring change being controlled.

BACKGROUND

As to a compound having a phenolic hydroxyl group to be used in the present invention, a compound of the formula (I):

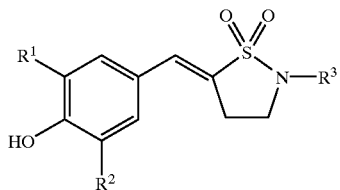

wherein $R^1$ and $R^2$ each is independently hydrogen, low alkyl or low alkyloxy; $R^3$ is hydrogen, low alkyl, cycloalkyl, lower alkyloxy, arylalkyloxy, heteroarylalkyloxy, lower alkylcarbonyl, arylcarbonyl, substituted or unsubstituted carbamoyl or a group of the formula: —$(CH_2)_n$—Q wherein Q is hydroxy, substituted or unsubstituted amino, aryl, heteroaryl, carboxy or low alkyloxycarbonyl; and n is an integer of 0–3, its pharmaceutically acceptable salt or a hydrate thereof (hereinafter referred to as a compound (I)) is disclosed in Japanese Patent Publication (Kokai) No. 211819/1994, and is known to be useful as an anti-inflammatory agent.

The compound (I) known as a non-steroid type anti-inflammatory agent is very useful because it is a selective inhibitor against cyclooxygenase II which does not have the side effects caused by inhibiting cyclooxygenase I.

Because the compound (I) is hardly soluble in water, it must be formulated through wet granulation process using a water-soluble high molecular compound or a surface-active agent with a high HLB value for making the surface of the compound hydrophilic in order to enhance the absorbability or solubility. But the present inventors have found that a granulation product of the compound (I) such as a wet composition in wet granulation process, a dried granule in drying process or the like, shows coloring change under a high humidity condition and a pharmaceutical composition shows coloring change, while stored under warming and humidification.

Generally, as a method for masking the coloring change of a pharmaceutical composition, a physical method such as adding a coloring agent, coating a tablet, masking a particle of a compound or the like is used. Each method is complicated to increase the production cost.

As a specific method for controlling the coloring change depending on the nature of each compound, known is a method for controlling the coloring change of a solution comprising uracil derivatives by using a metal salt of formaldehyde sulfoxyl acid, described in Japanese Patent Publication (Kokai) No. 102415/1977, or a method for controlling the coloring change of a granulation product comprising ascorbic acid by using an organic solid acid, described in Japanese Patent Publication (Kokai) No. 47121/1991. A method for controlling coloring change of a pharmaceutical composition containing a compound having a phenolic hydroxy group has not been reported.

DISCLOSURE OF INVENTION

The present invention provides a pharmaceutical composition containing a compound having a phenolic hydroxy group, in detail an anti-inflammatory agent or an antioxidant having a phenolic hydroxyl group, and in more detail a compound (I) with coloring change being controlled.

BEST MODE FOR CARRYING OUT THE INVENTION

Figure 1:
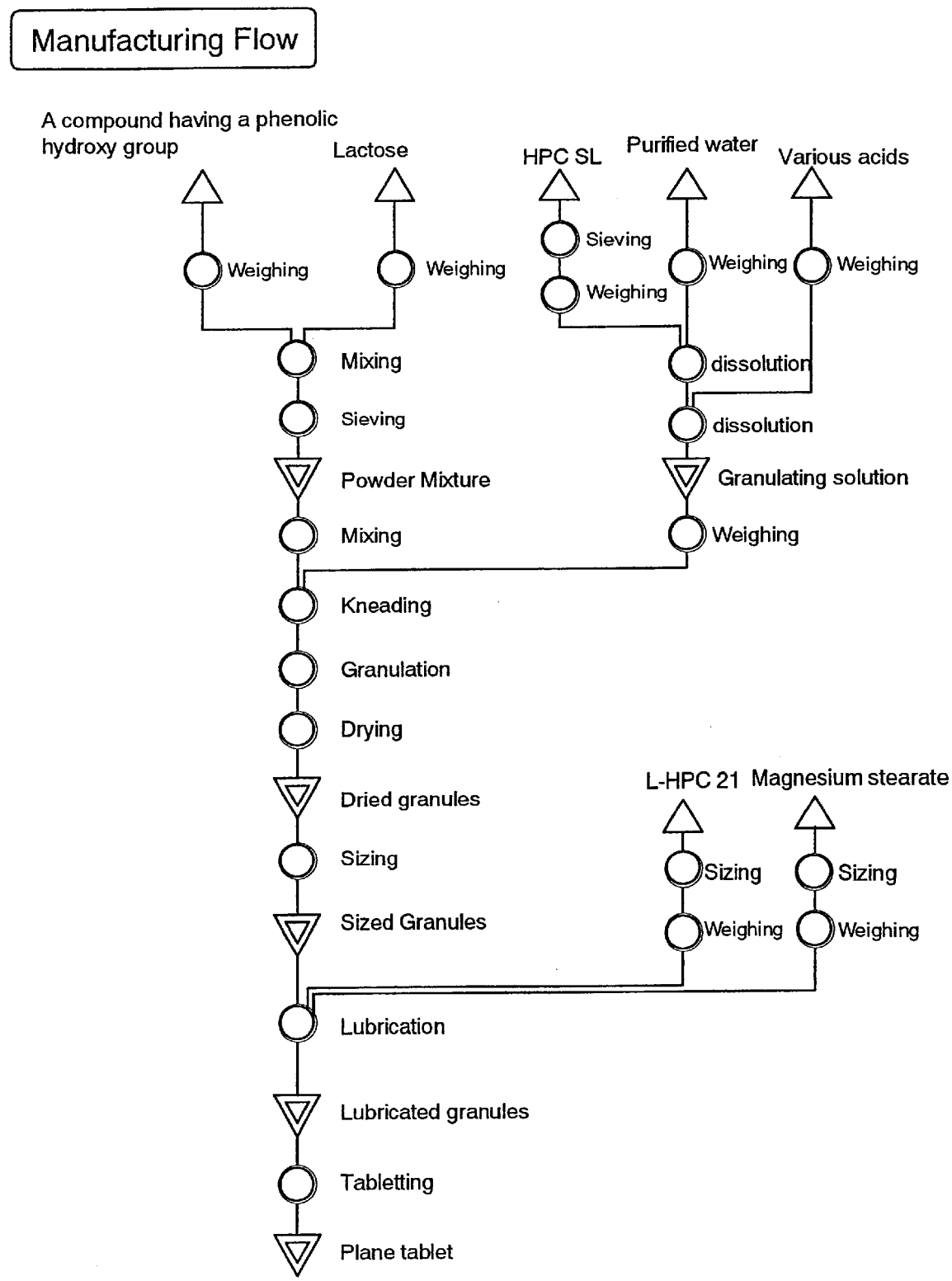
FIG. 1 shows an example of a process for manufacturing a pharmaceutical composition containing a compound having a phenolic hydroxy group with coloring change being controlled.

The present inventors have intensively researched the cause of coloring change of a compound having a phenolic hydroxy group, in detail an anti-inflammatory agent or an antioxidant having a phenolic hydroxyl group, and in more detail a compound (I), to suppose that the coloring change is caused by the formation of a conjugating quinoide due to the dissociation of a proton of a phenolic hydroxy group under a high humidity condition, and found that a highly stable pharmaceutical composition without coloring change can be obtained by adding an acid for controlling the dissociation of the proton to a binder solution in a wet granulation process to accomplish the present invention.

The present invention provides:

1) a pharmaceutical composition which comprises a compound having a phenolic hydroxy group and an acid wherein coloring change is controlled,
2) the pharmaceutical composition according to the above 1) wherein said acid is an organic acid or an inorganic acid,
3) the pharmaceutical composition according to the above 1) wherein said acid is phosphoric acid, citric acid, succinic acid and/or malic acid,
4) the pharmaceutical composition according to the above 1) wherein said compound having a phenolic hydroxy group is an anti-inflammatory agent or an antioxidant having a phenolic hydroxyl group,
5) the pharmaceutical composition according to the above 1) wherein said compound having a phenolic hydroxy group is a compound of the formula (I):

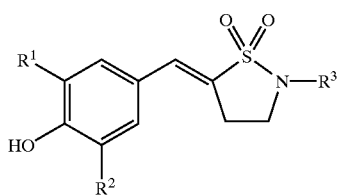

wherein R¹ and R² each is independently hydrogen, low alkyl or low alkyloxy; R³ is hydrogen, low alkyl, cycloalkyl, lower alkyloxy, arylalkyloxy, heteroarylalkyloxy, lower alkylcarbonyl, arylcarbonyl, substituted or unsubstituted carbamoyl or a group of the formula: —(CH$_2$)$_n$—Q wherein Q is hydroxy, substituted or unsubstituted amino, aryl, heteroaryl, carboxy or low alkyloxycarbonyl; and n is an integer of 0–3, its pharmaceutically acceptable salt or a hydrate thereof, 6) the pharmaceutical composition according to the above 1) wherein said compound having a phenolic hydroxy group is (E)-2-ethyl-5-(3,5-di-tert-butyl-4-hydroxy)benzylidene-1,2-isothiazolidine-1,1-dioxide, its pharmaceutically acceptable salt or a hydrate thereof, 7) the pharmaceutical composition according to any one of the above 1) to 6) wherein the amount of said acid is 0.1 to 10% by the weight to the compound having a phenolic hydroxyl group, 8) the pharmaceutical composition according to any one of the above 1) to 7) wherein said pharmaceutical composition is a solid composition, and 9) the pharmaceutical composition according to any one of the above 1) to 7) wherein said pharmaceutical composition is a tablet.

Additionally, the present invention provides:

10) a method for manufacturing a pharmaceutical composition containing a compound having a phenolic hydroxy group with coloring change being controlled, which comprises adding an acid to said composition, and 11) a method for controlling coloring change of a pharmaceutical composition containing a compound having a phenolic hydroxy group, which comprises adding an acid to said composition.

The coloring change of a pharmaceutical composition containing a compound having a phenolic hydroxyl group is thought to be based on the nature of a phenolic hydroxyl group. A phenolic hydroxyl group is known to show the following equilibrium for example. Under high humidity, the equilibrium between each compound shifts to the right formula, its keto form. The change of phenol structure from enol form to keto form, giving the conjugated quinoide form, causes the coloring change of a pharmaceutical composition such as a granulation product or a tablet.

In the field of analytical reagents, the following examples are known as positively utilizing the change from enol form to keto form, coloring change based on formation of its quinoide form.

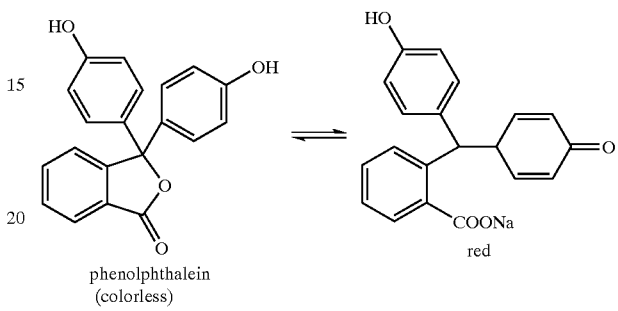

phenolphthalein (colorless)     red

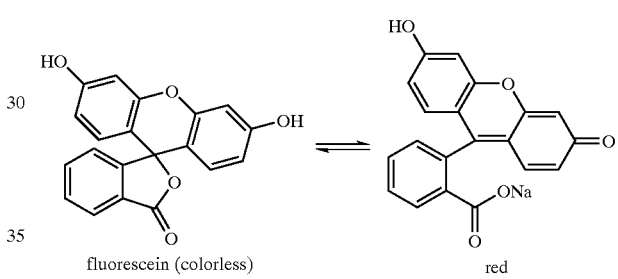

fluorescein (colorless)     red

This phenomenon is found in a compound having a phenolic hydroxyl group. The compound (I) can form its quinoide form illustrated at the right of the following scheme.

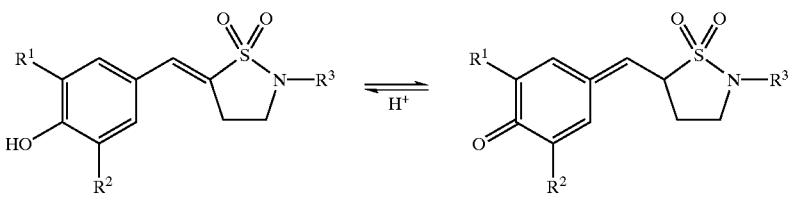

However, it is necessary to manufacture a pharmaceutical composition without its coloring change, especially that containing a compound having a phenolic hydroxy group.

The present invention provides a very stable pharmaceutical composition without coloring change by adding an acid for controlling the dissociation of a proton in a manufacturing process so as to shift the above equilibrium to the left, its phenol structure of enol form.

The present invention can be carried out regardless of the kinds of acids. Preferred is an organic acid and an inorganic acid. Preferred examples of the organic acid include citric acid, succinic acid, malic acid and the like. Preferred examples of the inorganic acid include phosphoric acid and the like.

Although the quantity of the acid contained in a pharmaceutical composition depends on the kinds of the acid to be used or the embodiment of a pharmaceutical composition, preferred is 0.01 to 20% (W/W), especially 0.1 to 10% (W/W).

The present invention can be carried out regardless of the kinds of compounds, if the compound has a phenolic hydroxyl group. Examples of the compound having a phenolic hydroxyl group include hesperidin, tyrosine, dopamine, methyldopa, norepinephrine, epinephrine, trimetoquinol, flopropione, isoprenaline, morphine, heteromethylmorphine, nalorphine, BF-389, CI-1004, the compound (I), BHT and the like.

A Preferred example of the compound having a phenolic hydroxyl group is an anti-inflammatory agent or an antioxidant having a phenolic hydroxyl group. Many anti-inflammatory agents or antioxidant agents are known as having a phenolic hydroxyl group. Examples of such an anti-inflammatory agent include BF-389, CI-1004, the compound (I) and the like. More preferred is the compound (I). Most preferred is the compound (I) wherein $R^1$ and $R^2$ each is tert-butyl and $R^3$ is ethyl, (E)-2-ethyl-5-(3,5-di-tert-butyl-4-hydroxy)benzylidene-1,2-isothiazolidine-1,1-dioxide. Examples of such an antioxidant include BHT and the like. The structures of each compound are shown below.

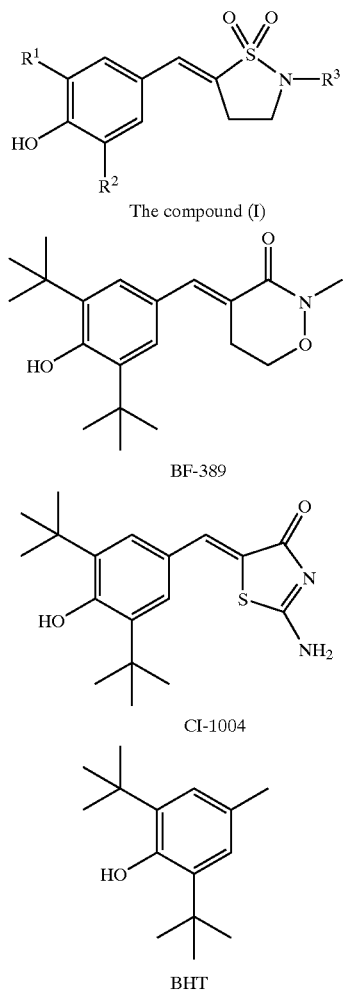

a manufacture granule, a manufacture powder, a solid composition such as a tablet, a granule, a coating agent, a powder, a circle agent or the like.

The term "low alkyl" includes a straight or branched $C_1$–$C_8$ alkyl group, for example, methyl, ethyl, n-propyl, isopropyl, n-butyl, isobutyl, sec-butyl, tert-butyl, n-pentyl, isopentyl, neopentyl, sec-pentyl, tert-pentyl, n-hexyl, neohexyl, isohexyl, sec-hexyl, tert-hexyl, heptyl and octyl. Preferred is a straight or branched $C_1$–$C_4$ alkyl group, for example, methyl, ethyl or tert-butyl.

The term "low alkyloxy" includes a straight or branch $C_1$–$C_6$ alkyloxy, for example, methoxy, ethoxy, n-propoxy, isopropoxy, n-butoxy, isobutoxy, sec-butoxy, tert-butoxy, n-pentyloxy, isopentyloxy, neopentyloxy, sec-pentyloxy, tert-pentyloxy, n-hexyloxy, neo hexyloxy, isohexyloxy, sec-hexyloxy, tert-hexyloxy and the like. Preferred is $C_1$–$C_4$ alkyloxy, for example, methoxy.

The term "cycloalkyl" includes a $C_3$–$C_7$ cycloalkyl group, for example, cyclopropyl, cyclobutyl, cyclopentyl, cyclohexyl, cycloheptyl and the like. Preferred is a $C_3$–$C_5$ cycloalkyl.

The term "aryl" includes unsubstituted or substituted phenyl and unsubstituted or substituted naphthyl, and the substituent is one or more selected from halogen, low alkyloxy, low alkyl, nitro and the like. Examples of "aryl" include phenyl, 4-chlorophenyl, 4-methoxyphenyl, 4-nitrophenyl, 3,4-dichlorophenyl, 3,4-dimethoxyphenyl, 3,4-dinitrophenyl, 1-naphthyl, 2-naphthyl and the like.

The term "arylalkyloxy" includes the above "lower alkyloxy" substituted with the above "aryl", for example, benzyloxy, 4-chlorobenzyloxy, 4-methoxybenzyloxy, 3,4-dichlorobenzyloxy, 3,4-dimethoxybenzyloxy, 4-nitrobenzyloxy, 2-phenylethyloxy, 2-(4-chlorophenyl)ethyloxy, 2-(4-methoxyphenyl)ethyloxy, 1-naphthylmethyloxy, 2-naphthylmethyloxy and the like. Preferred is benzyloxy.

The term "heteroaryl" includes a substituted or unsubstituted aromatic heterocyclic group containing 1–4 hetero atom(s), for example, pyridyl, thiazolyl, isothiazolyl, oxazolyl, isoxazolyl, imidazolyl, triazolyl, tetrazolyl and the like. The substituent includes halogen, amino, nitro, hydroxy, carboxy and the like. More preferred is pyridyl, thiazolyl, oxazolyl, imidazolyl. Most preferred is pyridyl.

The term "heteroarylalkyloxy" includes the above lower alkyloxy substituted with the above heteroaryl, for example, 2-pyridylmethyloxy, 3-pyridylmethyloxy, 4-pyridylmethyloxy, 2-imidazolylmethyloxy, 4-imidazolylmethyloxy, 2-thiazolylmethyloxy, 4-thiazolylmethyloxy and the like.

The term "low alkylcarbonyl" includes a carbonyl group substituted with the above lower alkyl, for example, acetyl, propionyl, butylyl, valeroyl, hexanoyl, heptanoyl, octanoyl and the like.

The term "arylcarbonyl" includes a carbonyl group substituted with the above aryl, for example, benzoyl, 4-chlorobenzoyl, 4-methoxybenzoyl, 4-nitrobenzoyl, 3,4-dichlorobenzoyl, 3,4-dimethoxybenzoyl, 3,4-dinitrobenzoyl, 1-naphthoyl, 2-naphthoyl and the like.

The term "substituted or unsubstituted carbamoyl" includes a carbamoyl group at the nitrogen atom optionally substituted with one or two substituent(s) which include(s) low alkyl, low alkyloxy, hydroxy, cycloalkyl, arylalkyl, alkyloxyalkyl, alkylcarbonyl, arylcarbonyl, cycloalkyloxy, arylalkyloxy and the like. Preferred examples of the substituent are low alkyl, low alkyloxy, hydroxy and the like. Examples of "substituted or unsubstituted carbamoyl" include N-methylcarbamoyl, N,N-dimethylcarbamoyl, Each term to be used in the present specification is explained below.

The term "pharmaceutical composition" includes a kneading product, a granulation product, a dryness granule, N-hydroxycarbamoyl, N-methyl-N-hydroxycarbamoyl, N-methoxycarbamoyl, N-methoxy-N-methylcarbamoyl, N-ethylcarbamoyl, N,N-diethylcarbamoyl, N-ethyl-N-hydroxycarbamoyl, N-propylcarbamoyl, N,N-dipropylcarbamoyl, N-propyl-N-hydroxycarbamoyl and the like.

The term "low alkyloxycarbonyl" includes carbonyl substituted with the above low alkyloxy, for example, methoxycarbonyl, ethoxycarbonyl, propoxycarbonyl, isopropoxycarbonyl, butoxycarbonyl, isobutoxycarbonyl, tert-butoxycarbonyl and the like.

The term "substituted amino" includes mono- or di-substituted amino. Examples of the substituent(s) include low alkyl, arylalkyl and the like.

The term "its pharmaceutically acceptable salt or a hydrate thereof" includes a salt or a hydrate of the compound (I) (for example, the compound wherein R3-is a group of the formula: —(CH$_2$)$_n$—Q wherein Q is substituted or unsubstituted amino or carboxy; and n is an integer of 0–3), which is substantially non-toxic against a living thing. Examples of the pharmaceutically acceptable salt include a salt formed by reacting the compound (I) with an inorganic or organic acid or base. Such a salt is known as an acid addition salt and a base addition salt.

The compound (I) to be used in the present invention can be prepared in accordance with the method described in Japanese Patent Application Publication No. 211819/1994.

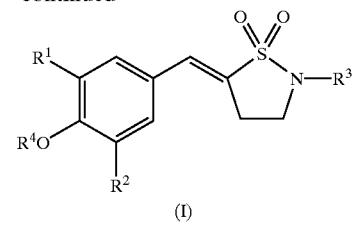

(I)

wherein $R^1$ and $R^2$ each is independently hydrogen, low alkyl or low alkyloxy; $R^3$ is hydrogen, low alkyl, cycloalkyl, lower alkyloxy, arylalkyloxy, heteroarylalkyloxy, lower alkylcarbonyl, arylcarbonyl, substituted or unsubstituted carbamoyl or a group of the formula: —(CH$_2$)$_n$—Q wherein Q is hydroxy, substituted or unsubstituted amino, aryl, heteroaryl, carboxy or low alkyloxycarbonyl; n is an integer of 0–3; and $R^4$ is hydroxy or a protective group of hydroxy.

When $R^4$ is a protective group of hydroxy, preferred examples of the protective group include methoxymethyl, methoxyethoxymethyl, trimethylsilyl, tert-butyldimethylsilyl or the like. More preferred is methoxymethyl.

Preparation procedure A

3-Chloropropylsulfonyl chloride (1) is reacted with amine (2) to yield sulfonamide intermediate (3). The reaction is carried out in the presence of base (A), if necessary, in a Preparation procedure A

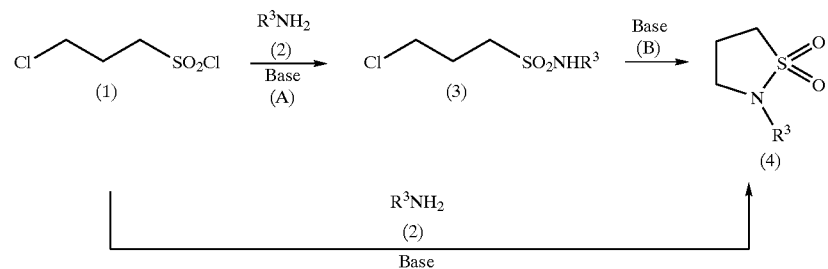

Preparation procedure B

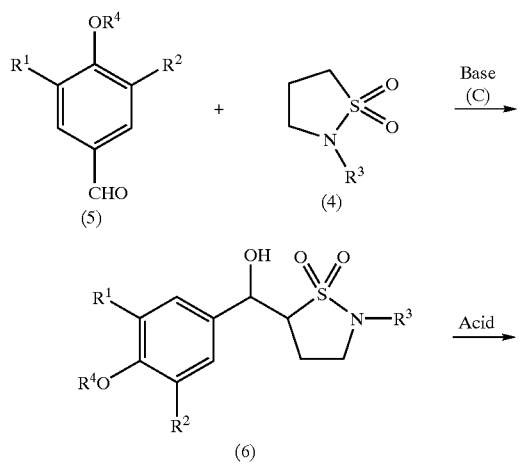

solvent such as ether, chloroform, methylene chloride, dichloroethane, tetrahydrofuran, dimethoxyethane, diethoxyethane, benzene, toluene, xylene, ethyl acetate, methyl acetate and the like, which solvent may contain water. The amine (R$^3$NH$_2$) may be in the form of hydrochloride salt. The base (A) used in the case of necessity includes alkali metal bases such as lithium hydroxide, sodium hydroxide, potassium hydroxide, sodium carbonate, potassium carbonate, sodium bicarbonate, potassium hydrogencarbonate and the like, and organic bases such as pyridine, 4-N,N-dimethylaminepyridine (DMAP), triethylamine, diisobutylethylamine, 1,8-diazabicyclo[5,4,0]undec-7-ene (DBU), 1,4-diazabicyclo[2,2,2]octane (DABCO) and the like. When an alkali metal base is used, it is preferable to add a phase transfer catalyst, if necessary. Examples of preferred phase transfer catalysts are quaternary ammonium salts such as N-benzyltrimethylammonium salts, tetrabutylammonium salts and the like.

The reaction for converting sulfonamide intermediate (3) into sulfur-containing heterocyclic compound (4) can be carried out in the presence of a base (B) in a solvent as described above, while anhydrous solvents such as dimethyl sulfoxide, dimethylformamide and the like may be also be used and rather preferable. Sodium hydride and lithium hydride can be used as a base (B) as well as those described above.

Alternatively, sulfur-containing compound (4) can be prepared directly from compound (1) without separation of sulfonamide intermediate (3). In this case, the reaction of compound (1) with amine (2) is carried out in a suitable solvent in the presence of two equivalents of a base. The solvent and the base may be selected from those exemplified above but it is particularly preferable to use sodium hydride as a base and dimethylformamide as a solvent.

Preparation Procedure B

The aldol reaction between compound (5) and compound (4) prepared in Preparation procedure A is carried out in the presence of a base (C) in a suitable solvent. Examples of a base (C) include organic lithium salts such as n-butyllithium, sec-butyllithium, tert-butyllithium, phenyllithium, lithium diisopropylamide, lithium diethylamide, lithium hexamethyldisilazane and potassium tert-butoxide and the like. Particularly, lithium diisopropylamide or lithium hexamethyldisilazane is preferable.

Example of reaction solvents include ether solvents such as diethyl ether, tetrahydrofuran (THF), dimethoxyethane, diethoxyethane and the like. The reaction is preferably conducted in the lithium metal, for example tetramethylethylenediamine, hexamethylphosphoramide and the like, if necessary.

The reaction is carried out at temperature ranging from $-80°$ C. to $+50°$ C. with preference in lower temperature range.

Aldol adduct (6) is converted to compound (I) in the presence of an acid. Examples of acids include organic acids such as trifluoroacetic acid, p-toluenesulfonic acid, camphorsulfonic acid and the like and inorganic acids such as sulfuric acid, hydrochloric acid and the like. Further, ordinary dehydrating agents such as thionyl chloride, methanesulfonyl chloride, aluminium chloride, phosphorus oxychloride, phosphorus pentachloride and the like can be used. Preferably, the reaction is carried out with heating in an aromatic hydrocarbon such as benzene, toluene, xylene and the like, a halogenated hydrocarbon such as chloroform, dichloromethane, dichloroethane and the like, or an ether solvent such as tetrahydrofuran, dimethoxyethane, diethoxyethane and the like.

Although example of preparation of the compound (I) to be used in the present invention is explained, the scope of the present invention is not limited to the following example.

Preparation Procedure Aa

N-Ethyl-1,2-isothiazolidine-1,1-dioxide (4a)

To a solution of 3-chloropropylsulfonyl chloride (1) (6.1 g, 34.5 mmol) in ether (25 ml) was dropwise added ethylamine (2a) (a 70% aqueous solution, 4.4 g, 68.3 mmol) with stirring and ice-cooling over 15 minutes, and the resultant mixture was stirred for one hour at room temperature. The reaction mixture was concentrated in vacuo, Benzene (100 ml) was added to the residue, and the solvent was removed in vacuo. To the residue was added ether (150 ml) and filtered to remove the insoluble material. The filtrate was distilled in vacuo to remove ether and 6.96 g (yield, about 100%) of crude N-ethyl-3-chloro propylsulfonamide (intermediate 3a) was obtained as colorless crystals (m.p.= $30-32°$ C.). To a solution of this intermediate (3a) (6.96 g, 34.5 mmol) in THF (50 ml) was slowly added sodium hydride (60% in oil, 1.52 g, 38.0 mmol) with stirring under ice-cooling over 15 minutes. To reaction mixture was stirred for another 30 minutes at room temperature. After the addition of the ether (50 ml), the mixture was filtered to remove insoluble material and solvent was distilled in vacuo to gi 4.93 g (96%) of the desired compound 4a as a pale yellow oil. IR (CH$_3$Cl) cm$^{-1}$: 3018, 2976, 2868, 1452, 1306, 1220, 1179, 1129, 1015; NMR (CDCl3)δ: 1.24 (3H, t, J=7.4 Hz), 2.28–2.42 (2H, m, CH$_2$), 3.10 (2H, q, J=7.4 Hz, CH$_2$), 3.15 (2H, t, J=7.6 Hz, CH$_2$), 3.22–3.29 (2H, m, CH$_2$).

Preparation Procedure Ba (E)-2-ethyl-5-(3,5-di-tert-butyl-4-hydroxy)benzylidene-1,2-isothiazolidinre-1,1-dioxide (I-1)

To diisopropylamine (15.5 ml, 110.6 mmol) was dropwise added in an ice-water bath n-butyllithium in n-hexane (1.6 M, 69.5 ml, 111 mmol) over 20 minutes with stirring was conducted for another 15 minutes. The reaction mixture was cooled was dropwise added a solution of N-ethyl-1,2-isothiazolidine-1,1-dioxide (4a) (15 g, 100.5 mmol), 3,5-di-tert-butyl-4-methoxymethylbenzaldehyde (5a) (25 g, 90.5 mmol) and HMPA (30 ml) in the THF (70 ml) over 15 minutes with stirring. The reaction mixture was stirred for another 30 minutes at the same temperature, warmed to room temperature, poured into cold 2N HCl (100 ml) and extracted with washed with a dilute aqueous solution (300 ml), dried over anhydrous sodium sulfate. The solvent was removed in vacuo, and the residue was subjected to column chromatography on silica gel eluting with n-hexanelethyl acetate (4:1 to 1:1) to give 21.3 g (55%) of aldol adduct (6a) as a colorless solid.

To a solution of the aldol adduct (6a) (8.5 g, 19.9 mmol) in toluene (150 ml) was added p-toluenesulfonic acid hydrate (2.49 g, 13 mmol). The resultant mixture was heated to reflux for 30 minutes and then poured into a dilute aqueous solution of sodium bicarbonate (150 ml) and extracted with washed ethyl acetate (150 ml×2). The organic layer washed with water (150 ml) and a saturated brine (150 ml), dried over anhydrous sodium sulfate. The solvent was removed in vacuo, and the residue was subjected to column chromatography on silica gel. From the fraction eluted with n-hexane/ethyl acetate (3:1), the desired compound (I-1) (2.59g, 36%) was yielded. M.p.=135–137° C. IR(KBr) cm$^{-1}$: 3610, 3440, 2970, 2880, 1645, 1597, 1430, 1290, 1173, 1151, 1139. NMR(CDCl$_3$)δ: 1.29 (3H, t, J=7.2 Hz, CH$_3$), 1.45 (18H, s, 2×But), 3.07–3.19 (4H, m, CH$_2$), 3.28 (2H, q, J=7.2 Hz, CH$_2$), 5.50 (1H, s, OH), 7.24–7.26 (3H, m, 2×Aromatic H, CH). Elementary analysis (C$_{20}$H$_{31}$NO$_3$S) Calcd: C, 65.71; H, 8.56; N, 3.83; S, 8.77. Found: C, 65.65; H, 8.43; N, 3.85; S, 8.78.

A method for manufacturing a pharmaceutical composition containing a compound having a phenolic hydroxy group with coloring change being controlled, includes the following methods.

(a) A granulating method comprising the step of circulating a compound having a phenolic hydroxy group under spraying a binder solution containing an acid in fluidized-bed granulation equipment.

(b) A granulating method comprising the step of circulating a mixture of a compound having a phenolic hydroxy group and an acid under spraying a binder solution in fluidized-bed granulation equipment.

(c) A granulating method comprising the step of kneading a mixture of a binder solution containing an acid and a compound having a phenolic hydroxy group in kneading equipment.

(d) A granulating method comprising the step of mixing a compound having a phenolic hydroxy group and an acid and adding a binder solution in kneading equipment.

Besides the above-mentioned methods, usual granulating methods can be used. An acid is dissolved in a binder solution in the above method (a) or (c). An acid is mixed with a compound having a phenolic hydroxy group in the above method (b) or (d). Preferred is method (c), illustrated in FIG. 1.

The amount of an acid to be contained in a pharmaceutical composition, depending on the kinds of acids to be used or the amount of a compound, is suitably chosen. In method (a) or (c), the addition amount of the acid is preferably adjusted to make the pH of a binder solution 2 to 3. The pH value of a binder solution depends on the kinds of binders.

Any binder for usual solid pharmaceutical compositions can be used for manufacturing the pharmaceutical composition of the present invention. The binder is an agent which is used in the production of solid compositions such as pills and tablets, for binding powders of medicine or excipients so as to keep the stiffness and appearance suitable. Preferred are water-soluble binders.

Examples of water-soluble binders include starch paste, pregelatinized starch, water-soluble cellulose, a water-soluble high molecular compound and the like. Preferred is water-soluble cellulose.

Examples of water-soluble celluloses include hydroxypropylcellulose, hydroxymethylcellulose, hydroxypropylmethylcellulose, carboxymethylcellulose, methyl cellulose and the like.

Examples of water-soluble high molecular compounds include polyvinylpyridone, dextrin and the like.

These binders can be used in a range of 0.12 to 4.8% (W/W), preferably 0.6 to 3.0%, and more preferably 1.2 to 1.8% to the total amount of a pharmaceutical composition.

The pharmaceutical composition of the present invention can be glanulated to a desired particle size and made into a fine subtilae or a granule after granulation. The obtained dried fine subtilae or granule can be mixed with a lubricant and the like to prepare a manufacturing powder, which is tableted to give a tablet.

The pharmaceutical composition may include other stabilizers, excipients and the like.

The present invention is concretely explained below. An acid to be used in the following example is phosphoric acid or citric acid. The compound (I) means (E)-2-ethyl-5-(3,5-di-tert-butyl-4-hydroxy)benzylidene-1,2-isothiazolidine-1,1-dioxide. Although the following examples are carried out in accordance with the above-mentioned method (c), the granulating method of the present invention is not limited to method (c).

In the following examples, HPC means hydroxypropylcelulose and SL means its grade. LHPC means low-substituted hydroxypropylcellulose. StMg means magnesium stearate.

EXAMPLE 1

Formulation Prepared by Using a Binder Solution of Various pH Value

Binder solutions of various pH values (pH=1.2, 1.5, 2.1, 3.0, 3.7) were prepared by adding phosphoric acid to a HPC SL water solution (12%) that is a binder solution for wet granulation. A binder solution of pH 6.1 was prepared without adding phosphoric acid. The above each solution and the compound I-1 was kneaded at the ratio of 1:2 (W/W) in mortar to give an undried granulation product.

EXAMPLE 2

Formulation Without Using an Acid

A mixed powder of the compound I-1 (50 g) and D-mannitol (164.9 g) was mixed by a low shaer mixer. A granulating solution containing HPC (3.5 g) was added thereto and the powder mixture was kneaded for 10 minutes, and granulated with 8 mesh SUS screen. The obtained granulation product was dried at 50° C. for 45 minutes by a Tray drier. The dried granules were sized by a sizing machine (produced by showa chemical machine, named powermil) with 30 mesh SUS screen. To the sized granule (200 g) were added LHPC (11.0 g) as disintegrant and StMg (8.8 g) as lubricant. The lubricated granules were compressed by a rotary tableting machine equipped with a mallet (8.0 mm ø) (produced by kikusui factory, named RTM-S30K-2S) to give tablets (weight: 240 mg, thickness: 4.4 mm per a tablet).

EXAMPLE 3

Formulation Containing Phosphoric Acid

A mixed powder of the compound I-1 (50 g) and D-mannitol (163.9 g) was mixed by a low shaer mixer. A granulating solution containing HPC (3.5 g) and phosphoric acid (1.0 g) was added thereto and the powder mixture was kneaded for 10 minutes, and granulated with 8 mesh SUS screen. The obtained granulation product was dried at 50° C. for 45 minutes by a Tray drier. The dried granules were sized by a sizing machine (produced by showa chemical machine, named powermil) with 30 mesh SUS screen. To the sized granule (200 g) were added LHPC (11.0 g) as disintegrant and StMg (8.8 g) as lubricant. The lubricated granules were compressed by a rotary tableting machine equipped with a mallet (8.0 mm ø) (produced by kikusui factory, named RTM-S30K-2S) to give tablets (weight: 240 mg, thickness: 4.4 mm per a tablet).

EXAMPLE 4

Formulation Containing Citric Acid

Tablets were prepared according to Example 3, by using citric acid in place of phosphoric acid.

Contents of the tablets manufactured in Examples 2 to 4 are shown in Table 1.

TABLE 1

| | Contents | | |
|---|---|---|---|
| | Formulation not containing an acid | Formulation containing phosphoric acid | Formulation containing citric acid |
| Compound (I) | 50.0 mg | 50.0 mg | 50.0 mg |
| D-mannitol | 164.9 | 163.9 | 163.9 |
| hydroxypropylcellulose | 3.5 | 3.5 | 3.5 |
| phosphoric acid | | 1.0 | |
| citric acid | | | 1.0 |
| low-substituted hydroxypropylcellulose | 12.0 | 12.0 | 12.0 |
| magnesium stearate | 9.6 | 9.6 | 9.6 |
| Total | 240.0 mg/T | 240.0 mg/T | 240.0 mg/T |

Examination 1

Relationship Between pH of a Binder Solution and Coloring Change of a Composition The dried granules manufactured in Example 1 were stored at 60° C. in a sealed container for four days. Coloring change of them was examined. Results are shown in Table 2.

TABLE 2

The amount of an acid to be added (pH of a binder solution) and coloring change of a composition

| Concentration of Phosphoric acid (%) | 0 | 0.03 | 0.2 | 0.3 | 3.0 | 6.0 |
|---|---|---|---|---|---|---|
| Amount per tablet | 0 | 0.1 | 0.67 | 1.0 | 10.0 | 20.0 |
| pH of a binder solution | 6.1 | 3.7 | 3.0 | 2.1 | 1.5 | 1.2 |
| coloring change | Red | pale red | no | no | Yellow | orange |

Examination 2

Coloring Change of the Composition

Tablets manufactured in Examples 2 to 4 were stored at 60° C. in a sealed glass container for two weeks. Each stability (coloring change) thereof was examined.

TABLE 3

Stability (Coloring Change)

| Storage Condition | Formulation not containing an acid | Formulation containing phosphoric acid | Formulation containing citric acid |
|---|---|---|---|
| 60° C. in a sealed glss container, 2 weeks | Red | no change | no change |

Industrial Applicability

A pharmaceutical composition prepared by the present invention is useful because its coloring change does not appear in the manufacturing process and it has good stability in appearance. Therefore, the present invention is useful for manufacturing a pharmaceutical composition containing a compound having a phenolic hydroxyl group with coloring change being controlled.

What is claimed is:

1. A pharmaceutical solid composition which comprises a compound having a phenolic hydroxy group and an acid wherein coloring change is controlled, wherein said compound having a phenolic hydroxyl group is a compound of formula I:

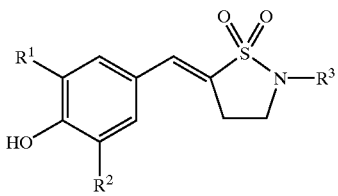

wherein $R^1$ and $R^2$ each is independently hydrogen, straight or branched $C_{1-8}$ alkyl, or straight or branched $C_{1-6}$ alkyloxy; $R^3$ is hydrogen, straight or branched $C_{1-8}$ alkyl, cycloalkyl, straight or branched $C_{1-6}$ alkyloxy, arylalkyloxy, heteroarylalkyloxy, straight or branched $C_{1-8}$ alkylcarbonyl, arylcarbonyl, substituted or unsubstituted carbamoyl, or a group of the formula: —$(CH_2)_n$—Q wherein Q is hydroxy, substituted or unsubstituted amino, aryl, heteroaryl, carboxy or straight or branched $C_{1-6}$ alkyloxycarbonyl; and n is an integer of 0–3; or a pharmaceutically acceptable salt or hydrate thereof, and wherein the amount of said acid is 0.1 to 10% by weight relative to the compound having the phenolic hydroxyl group.

2. The pharmaceutical solid composition according to claim 1 wherein said acid is an organic acid or an inorganic acid.

3. The pharmaceutical solid composition according to claim 1 wherein said acid is phosphoric acid, citric acid, succinic acid and/or malic acid.

4. The pharmaceutical solid composition according to claim 1 wherein said compound having a phenolic hydroxyl group is an anti-inflammatory agent or an antioxidant having a phenolic hydroxyl group.

5. The pharmaceutical solid composition according to claim 1 wherein said compound having a phenolic hydroxyl group is (E)-2-ethyl-5-(3,5-di-tert-butyl-4-hydroxy)benzyliden-1,2-isothiazolidin-1,1-dioxide, or a pharmaceutically acceptable salt or a hydrate thereof.

6. The pharmaceutical solid composition according to claim 1 wherein said pharmaceutical solid composition is a tablet.

7. A process for manufacturing a pharmaceutical solid composition comprising a compound having a phenolic hydroxyl group with coloring change being controlled, which comprises adding an acid to said composition, wherein said compound having a phenolic hydroxyl group is a compound of formula I:

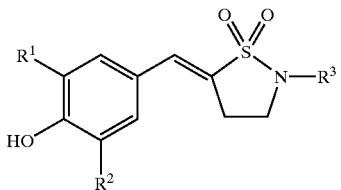

wherein $R^1$ and $R^2$ each is independently hydrogen, straight or branched $C_{1-8}$ alkyl, or straight or branched $C_{1-6}$ alkyloxy; $R^3$ is hydrogen, straight or branched $C_{1-8}$ alkyl, cycloalkyl, straight or branched $C_{1-6}$ alkyloxy, arylalkyloxy, heteroarylalkyloxy, straight or branched $C_{1-8}$ alkylcarbonyl, arylcarbonyl, substituted or unsubstituted carbamoyl, or a group of the formula: —$(CH_2)_n$—Q wherein Q is hydroxy, substituted or unsubstituted amino, aryl, heteroaryl, carboxy or straight or branched $C_{1-6}$ alkyloxycarbonyl; and n is an integer of 0–3; or a pharmaceutically acceptable salt or hydrate thereof, and wherein the amount of said acid is 0.1 to 10% by weight relative to the compound having the phenolic hydroxyl group.

8. A method for controlling coloring change of a pharmaceutical solid composition comprising a compound having a phenolic hydroxyl group, which comprises adding an acid to said composition, wherein the amount of said acid is 0.1 to 10% by weight relative to the compound having the phenolic hydroxyl group.

9. The process according to claim 7, wherein said compound having a phenolic hydroxyl group is (E)-2-ethyl-5-(3,5-di-tert-butyl-4-hydroxy)benzyliden-1,2-isothiazolidin-1,1-dioxide, or a pharmaceutically acceptable salt or a hydrate thereof.

10. The method according to claim 8, wherein said compound having a phenolic hydroxyl group is a compound of formula I:

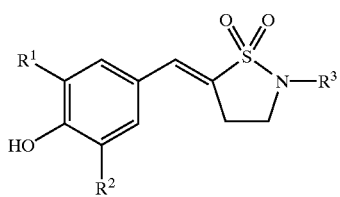

wherein R¹ and R² each is independently hydrogen, straight or branched $C_{1-8}$ alkyl, or straight or branched $C_{1-6}$ alkyloxy; R³ is hydrogen, straight or branched $C_{1-8}$ alkyl, cycloalkyl, straight or branched $C_{1-6}$ alkyloxy, arylalkyloxy, heteroarylalkyloxy, straight or branched $C_{1-8}$ alkylcarbonyl, arylcarbonyl, substituted or unsubstituted carbamoyl, or a group of the formula: —$(CH_2)_n$—Q wherein Q is hydroxy, substituted or unsubstituted amino, aryl, heteroaryl, carboxy or straight or branched $C_{1-6}$ alkyloxycarbonyl; and n is an integer of 0–3; or a pharmaceutically acceptable salt or hydrate thereof.

11. The method according to claim 8, wherein said compound having a phenolic hydroxyl group is (E)-2-ethyl-5-(3,5-di-tert-butyl-4-hydroxy)benzyliden-1,2-isothiazolidin-1,1-dioxide, or a pharmaceutically acceptable salt or a hydrate thereof.

* * * * *